(12) United States Patent
Shah et al.

(10) Patent No.: US 11,988,117 B2
(45) Date of Patent: May 21, 2024

(54) ENGINE LUBRICATION OIL CONSUMPTION AND CONDITION MONITORING

(71) Applicant: Caterpillar Energy Solutions GmbH, Mannheim (DE)

(72) Inventors: Darshit Shah, Baden-Württemberg (DE); Jan-Rudolf Spitzer, Mannheim (DE); Markus Frank, Mannheim (DE)

(73) Assignee: Caterpillar Energy Solutions GmbH, Mannheim (DE)

( * ) Notice: Subject to any disclaimer, the term of this patent is extended or adjusted under 35 U.S.C. 154(b) by 66 days.

(21) Appl. No.: 17/462,188

(22) Filed: Aug. 31, 2021

(65) Prior Publication Data

US 2022/0065142 A1 Mar. 3, 2022

(30) Foreign Application Priority Data

Sep. 2, 2020 (EP) .................................... 20194017

(51) Int. Cl.
*F01M 11/12* (2006.01)
*G01F 23/263* (2022.01)
*G01N 33/28* (2006.01)

(52) U.S. Cl.
CPC ........... *F01M 11/12* (2013.01); *G01F 23/263* (2013.01); *G01N 33/2888* (2013.01); *F01M 2250/00* (2013.01); *G01N 33/2847* (2013.01); *G01N 33/2858* (2013.01); *G01N 33/2876* (2013.01)

(58) Field of Classification Search
CPC .... F01M 11/12; G01F 23/263; G01B 33/2888
See application file for complete search history.

(56) References Cited

U.S. PATENT DOCUMENTS

| | | | |
|---|---|---|---|
| 6,443,006 B1 * | 9/2002 | Degrave | G01F 23/266 |
| | | | 73/304 C |
| 6,459,995 B1 | 10/2002 | Collister | |
| 6,580,366 B1 | 6/2003 | Engfehr | |
| 8,482,420 B2 | 7/2013 | Blossfeld | |
| 8,707,773 B2 | 4/2014 | Blossfeld | |
| 8,710,973 B2 | 4/2014 | Scheider | |
| 2004/0093150 A1 | 5/2004 | Arai | |
| 2008/0093173 A1 | 4/2008 | James | |
| 2010/0058847 A1 | 3/2010 | Benz | |
| 2010/0180663 A1 | 7/2010 | Sun | |

(Continued)

FOREIGN PATENT DOCUMENTS

| | | |
|---|---|---|
| CN | 204827597 U | 12/2015 |
| CN | 105065085 B | 11/2017 |

(Continued)

OTHER PUBLICATIONS

European Search Report related to European Patent Application No. 20194017; dated Apr. 9, 2021.

*Primary Examiner* — Kevin A Lathers

(57) ABSTRACT

The present invention pertains to a method of determining a lubrication oil condition of a stationary gas engine comprising the steps of retrieving a lubrication oil temperature information and retrieving a lubrication oil level information from a lubrication oil level sensor, wherein the lubrication oil level sensor is a capacitance sensor, and a step of normalizing a lubrication oil level information over the lubrication oil temperature information.

20 Claims, 8 Drawing Sheets

(56) References Cited

U.S. PATENT DOCUMENTS

| | | |
|---|---|---|
| 2013/0080022 A1 | 3/2013 | McDonald |
| 2013/0218399 A1 | 8/2013 | Demaison |
| 2015/0066332 A1 | 3/2015 | Leone |
| 2017/0102308 A1 | 4/2017 | Gillette, II |

FOREIGN PATENT DOCUMENTS

| | | | |
|---|---|---|---|
| EP | 1956203 | B1 | 6/2011 |
| GB | 2306660 | A | 5/1997 |
| JP | H05171911 | A | 7/1993 |

\* cited by examiner

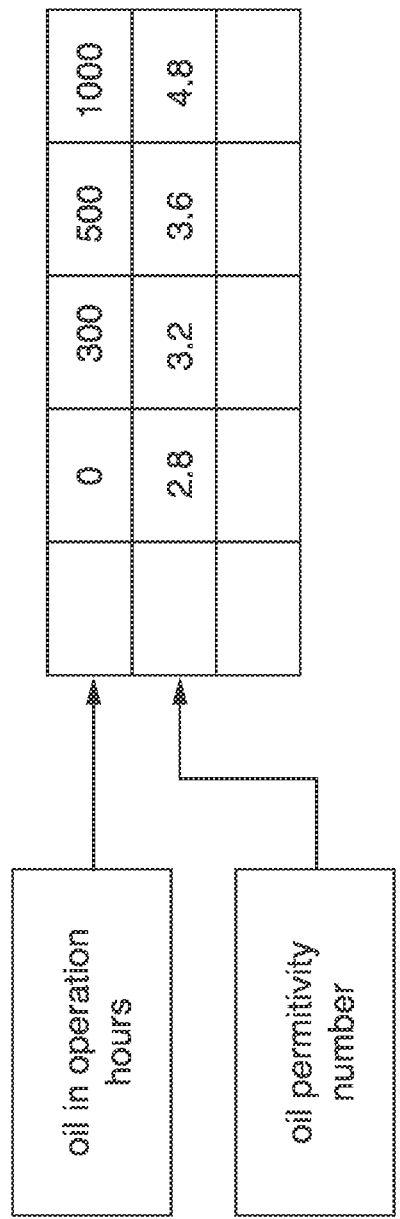
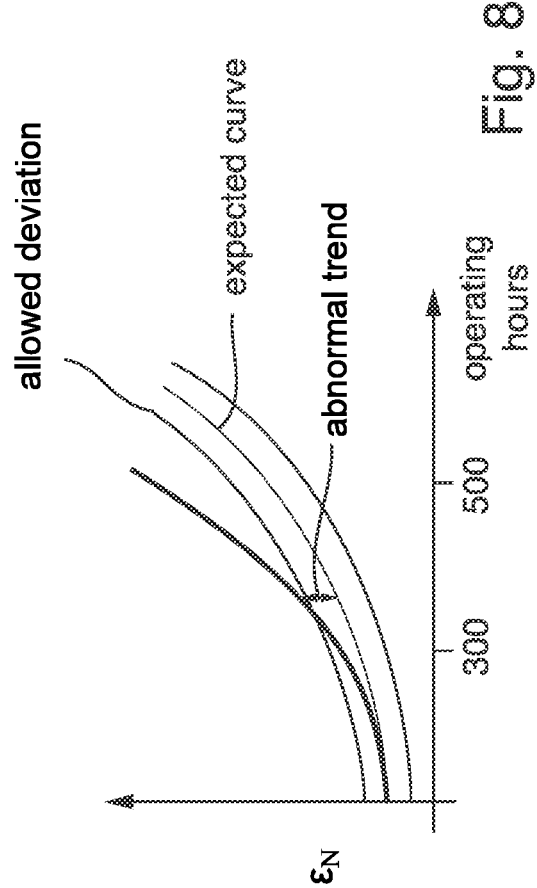
Fig. 8

ENGINE LUBRICATION OIL CONSUMPTION AND CONDITION MONITORING

TECHNICAL FIELD

The present invention relates to a method of determining a lubrication oil condition of a stationary gas engine. In addition, the present invention relates to a stationary gas engine comprising a non-transitory computer readable storage medium.

TECHNOLOGICAL BACKGROUND

Machine condition monitoring has become essential in maintaining and extending the health of reciprocating machinery, particularly in stationary gas engines. Real-time condition monitoring of a machine's health status can significantly reduce the operating cost by eliminating the need for costly machine shutdowns for inspection which would otherwise be needed to avoid the possibility of excessive component fatigue or failure during operation.

In terms of detecting health issues for mechanical components subjected to relative motion, the condition of engine lubrication oil is one of the parameters that provides extensive insights. In addition to the lubrication oil condition, also the lubrication oil consumption is a key indicator for component and engine health. Also, since lubrication oil changes result in engine downtime, it is important to determine a prognostic on lubrication oil remaining life. Being able to anticipate an upcoming engine revision or a lubrication oil change facilitates engine operation planning substantially. Monitoring lubrication oil parameters altogether helps avoiding unexpected downtime of the engine.

Over time, lubrication oil experiences degradation which is also called aging. The three main mechanisms that lead to lubrication oil aging are oxidation, water contamination and particle contamination.

As an example, referring to particle contamination, it is known that small wear debris particles with the sizes in the range of 1 to 10 μm are typically generated during normal wear machine operation, whereas abnormal wear generates particles larger than 10 μm. The particle population and size increases gradually with time until machine failure. Based on this trend, lubrication oil degradation due to particle contamination can be monitored by continuously analyzing the amount and size of the wear particles present in the lubrication oil.

Lubrication oil analysis has become an effective means to provide early warnings in the failure progression because it contains valuable information regarding the aging and damage of lubrication oil-wetted moving components.

To this end, dedicated lubrication oil quality sensors are known which are installed on the engine to monitor a portion of the lubricating lubrication oil from the continuously circulated lubrication flow in situ during operation.

However, although dedicated lubrication oil quality sensors can in fact provide comprehensive and detailed information about lubrication oil conditions, such dedicated sensors are expensive and are in many cases hard to retrofit to an existing stationary gas engine.

SUMMARY OF THE INVENTION

In view of the prior art, it is an objective to provide an improved method of determining a lubrication oil condition of a stationary gas engine in a simple, robust and cost effective way, preferably with the possibility of being retrofitted to an existing stationary gas engine. Additionally, it is an objective to provide a stationary gas engine in which the method is carried out.

This objective is solved by means of a method of determining a lubrication oil condition of a stationary gas engine with the features of claim 1 as well as a stationary gas engine with the features of claim 14. Preferred embodiments are set forth in the present specification, the figures as well as the dependent claims.

Accordingly, a method of determining a lubrication oil condition of a stationary gas engine is provided. The method comprises a step of retrieving a lubrication oil temperature information, a step of retrieving a lubrication oil level information from a lubrication oil level sensor, wherein the lubrication oil level sensor is a capacitance sensor, and a step of normalizing the lubrication oil level information over the lubrication oil temperature information.

Additionally, a stationary gas engine is provided, comprising at least one lubrication oil temperature sensor and at least one lubrication oil level sensor of the capacitance sensor type and a computing device and a non-transitory computer-readable storage medium encoded with data and instructions that, when executed by the computing device, cause the computing device to carry out the method.

BRIEF DESCRIPTION OF THE DRAWINGS

The present disclosure will be more readily appreciated by reference to the following detailed description when being considered in connection with the accompanying drawings in which:

FIG. 8 schematically shows a diagram illustrating determining an abnormal lubrication oil condition.

DETAILED DESCRIPTION OF PREFERRED EMBODIMENTS

Figure 1:
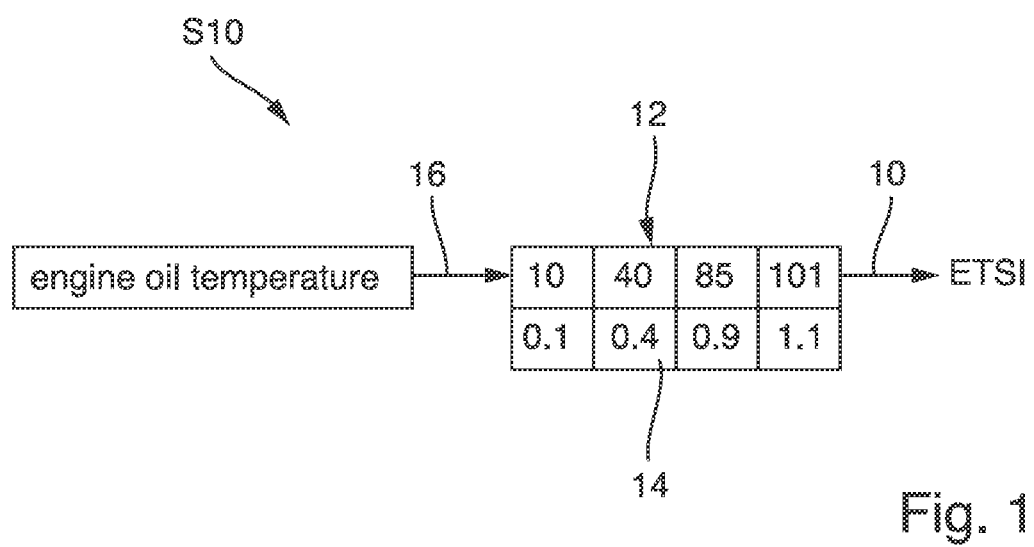
FIG. 1 schematically shows a diagram illustrating retrieving lubrication oil temperature information from an Engine Temperature State Indicator (ETSI) look-kip table.

In the following, the invention will be explained in more detail with reference to the accompanying figures. In the figures, like elements are denoted by identical reference numerals and repeated description thereof may be omitted in order to avoid redundancies.

FIG. 1 schematically shows a diagram illustrating retrieving lubrication oil temperature information 10 from an EFSI look-up table 12. The look-up table 12 comprises a first row containing reference engine lubrication oil temperature values as well as subsequent rows containing temperature reference values. The ETSI map 14, comprising all temperature reference values, may be populated based on engine cooling circuit design. In other words, the engine lubrication oil temperature signal 16, as measured in the engine, is not taken directly as lubrication oil temperature information 10, but instead a temperature reference value is retrieved from the ETSI look-up table 12 as lubrication oil temperature information 10. Hence, this value may be taken as lubrication oil temperature information 10 in the step of retrieving S10 the lubrication oil temperature information. As a result, the ETSI may be used as an enabler for the normalization step S30 (not shown in FIG. 1).

The term Engine Temperature State Indicator (ETSI) may equally be applied to temperatures of engines and lubrication oil reservoirs.

Figure 2:
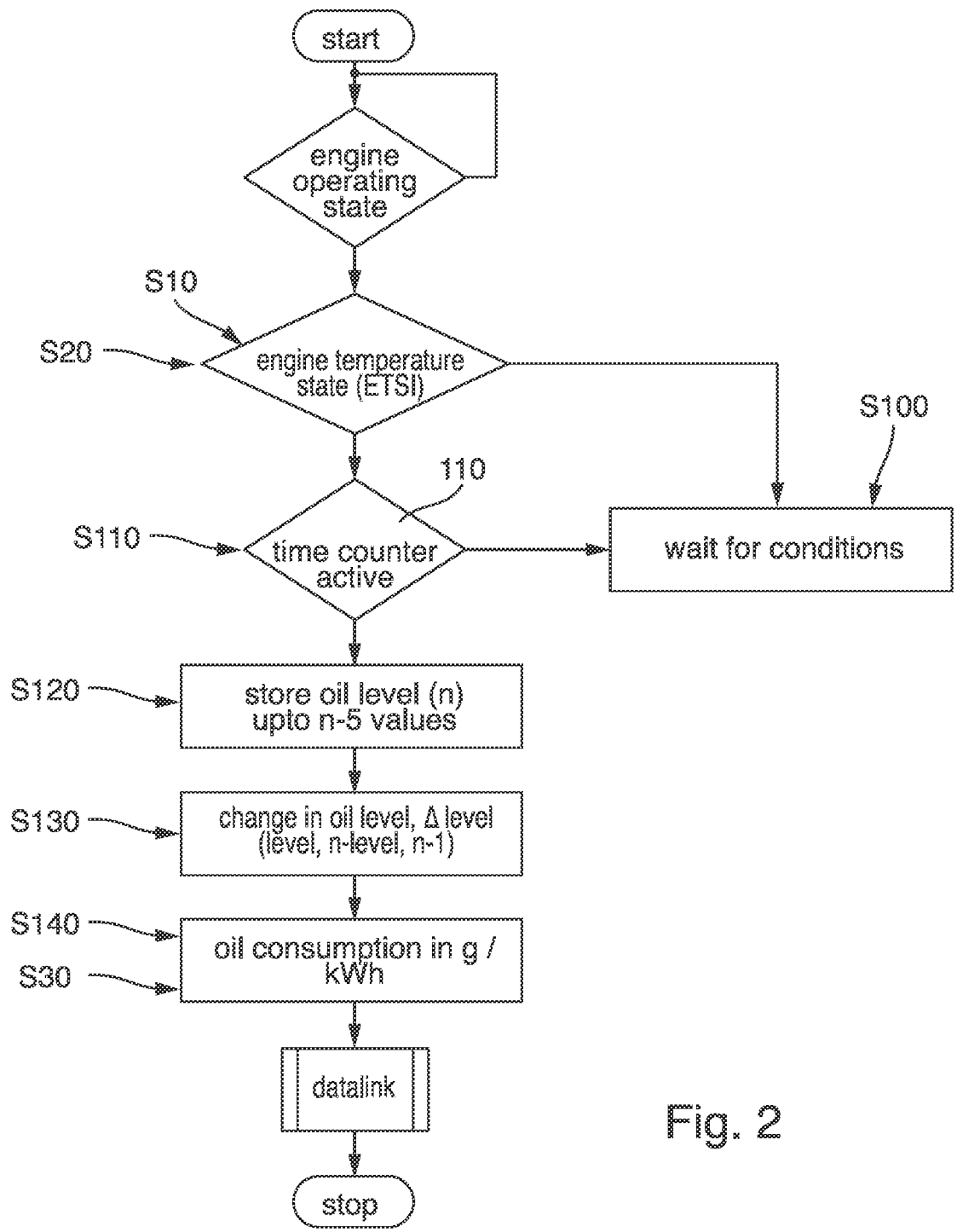
FIG. 2 schematically shows a flow diagram illustrating a method of determining a lubrication oil consumption.

FIG. 2 schematically shows a flow diagram illustrating a method of determining a lubrication oil consumption, Upon starting an engine, the operating state of the engine may be monitored, Once the engine is into running state, the algorithm represented in FIG. 2 may be active and may proceed to check the engine temperature state, which correlates with the engine lubrication oil temperature. More specifically, an ETSI information is retrieved in a retrieving step S10. In the shown embodiment, the retrieved ETSI value is then checked against a predetermined threshold during a waiting step S100.

Once the required thresholds for the ETSI value are reached, the algorithm according to FIG. 2 may wait for a counter 110 to be active. This counter 110 may be a simple function of time and may be calibrated to have values stored and processed at desired time intervals. At the same time, lubrication oil level information which is available as sensor output may be stored in a storing step S120.

The lubrication oil level information may be stored in a ring storage. According to the shown embodiment, the ring storage may for example save up to n values at a time and may work on a first in first out principle. Subsequently, a difference in lubrication oil level $\Delta L$ is determined in step S130 at a predefined time interval. The determined difference in lubrication oil level may also be stored. In step S140, the lubrication oil consumption is determined by utilizing a predetermined lubrication oil correlation.

The correlation may comprise a dependency between engine lubrication oil level to lubrication oil volume and further volume to weight. Further, a power producer counter may be provided using a generator power signal and operating hours. By that, the lubrication oil consumption may be calculated on the basis of g/kWh.

Figure 3:
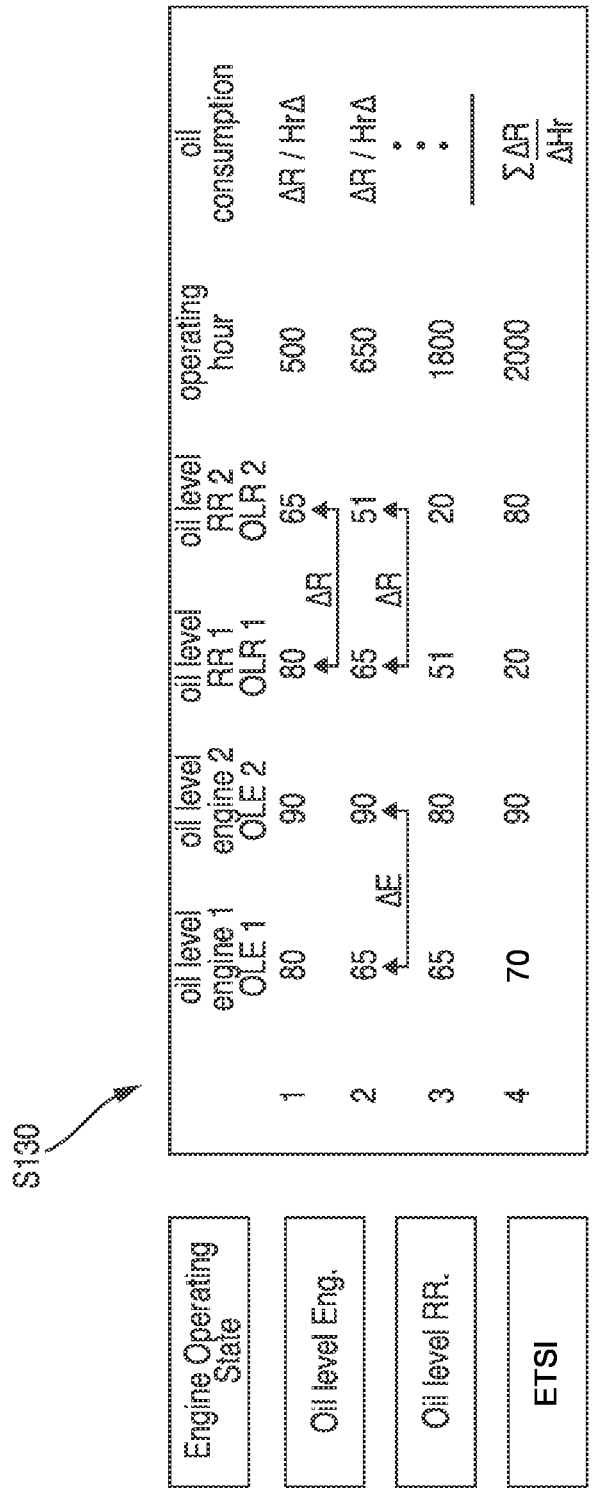
FIG. 3 schematically shows a diagram illustrating the calculation of lubrication oil level information.

FIG. 3 schematically shows a diagram illustrating the calculation of lubrication oil level information. Such a calculation may be applied in the step of determining S130 a difference in lubrication oil level at a predetermined time interval as discussed in FIG. 2. According to the example shown in FIG. 3, an engine and a lubrication oil reservoir are monitored in terms of their lubrication oil consumption. To this end, at least the input parameters a) engine operation state, b) lubrication oil level of the engine, c) lubrication oil level of the lubrication oil reservoir and d) the corresponding engine temperature state indicator ETSI information are taken as input parameters.

During a storing step, for example a storing step S120 as shown in FIG. 2, lubrication oil level information 20 may be stored per stop and start of the engine, hence two values of lubrication oil level information, namely lubrication oil level engine 1, OLE1, and lubrication oil level engine 2, OLE2, may be stored. Likewise, two values of lubrication oil level information are stored for the lubrication oil reservoir, namely lubrication oil level reserve 1, OLR1, and lubrication oil level reserve 2, OLR2.

Alternatively or additionally, during the storing step 120, lubrication oil level information 20 may be stored not only per stop and start of the engine, but also—or instead—based upon a predetermined condition such as an operating hours gap. To this end, those values of lubrication oil level information, taken from lubrication oil level engine 1, and lubrication oil level engine 2, may be stored. Likewise, said values of lubrication oil level information are stored for the lubrication oil reservoir.

As set forth in the table of FIG. 3, the operating hours of the engine are stored as well. Finally, the lubrication oil consumption may be calculated by taking into account the difference in lubrication oil level of the reservoir $\Delta R = OLR1 - OLR2$ and the operating hours relevant for this operation time period. The sum of all volumetric difference $\Sigma \Delta R$ divided by the relevant operating hours $\Delta Hr$ may then be converted in consumption of lubrication oil in g/kWh, provided that the density of the lubrication oil and the work produced was stored as well.

Figure 4:
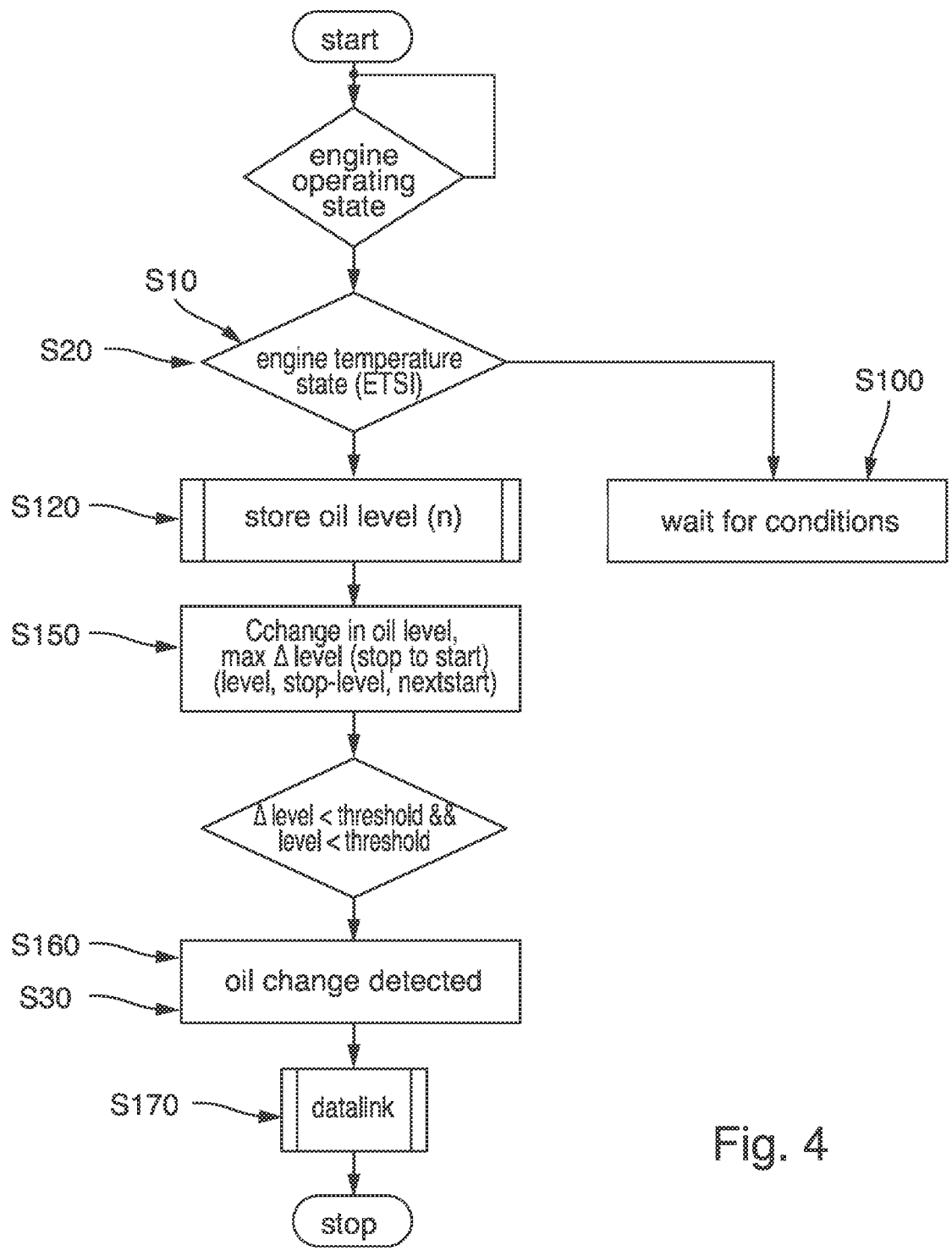
FIG. 4 schematically shows a flow diagram illustrating a method of determining a lubrication oil change detection.

FIG. 4 schematically shows a flow diagram illustrating a method of determining a lubrication oil change detection. According to the example shown in FIG. 4, an engine and a reservoir of lubrication oil are checked whether a lubrication oil change had occurred.

FIG. 4 schematically shows a flow diagram illustrating a method of determining a lubrication oil change detection. Upon starting an engine, the operating state of the engine may be monitored. Once the engine is into running state, the algorithm represented in FIG. 4 may be active and may proceed to check the engine temperature state, which correlates with the engine lubrication oil temperature. More specifically, an ETSI information is retrieved in a retrieving step S10. In the shown embodiment, the retrieved ETSI is then checked against a predetermined threshold during a waiting step S100. Subsequently, lubrication oil level information which is available as sensor output may be stored in a storing step S120.

In a monitoring step S150, a change in lubrication oil level between an engine stop condition until a subsequent engine start condition is monitored. In this step, it may continuously be checked whether the lubrication oil change had occurred between an engine stopped operating condition until a subsequent engine start condition. Possible parameters in the monitoring step S150 may for example be the change in lubrication oil level and the maximum difference in lubrication oil level $\Delta L$.

A lubrication oil change may be indicated, if the lubrication oil level in the engine or the lubrication oil reservoir was confirmed empty or almost empty during a stop of the engine. Hence, if during said start end stop conditions the lubrication oil level dropped below a predetermined threshold during the monitoring step S150, it may be indicated in indicating step S160 that a lubrication oil change had occurred. As an example, a lubrication oil change could be indicated, if the lubrication oil level engine one value fell below 10% of the initial lubrication oil level in the engine. Additionally or alternatively, a lubrication oil change may be indicated, if the lubrication oil level in the lubrication oil reservoir fell below 10% of its initial value. In this case, the method may comprise an indicating step S160, indicating, that a lubrication oil change had occurred.

Further, a counter for a subsequent lubrication oil change may be updated in updating step S170 which includes the normalizing step S30. Thereby, a lubrication oil life counter may be reset. By the same token, engine operating hours may be stored in the remaining operating hours till next lubrication oil change may be updated. Further, an updated remaining useful life (RUL) value of lubrication oil based on predefined life and operating hours for lubrication oil may be calculated in the updating step S170.

According to a further step, which is not shown in FIG. 4, a step of checking the lubrication oil level sensor for any active diagnostics or anomalies in order to qualify the lubrication oil change indication step S160 may be provided.

Figure 5:
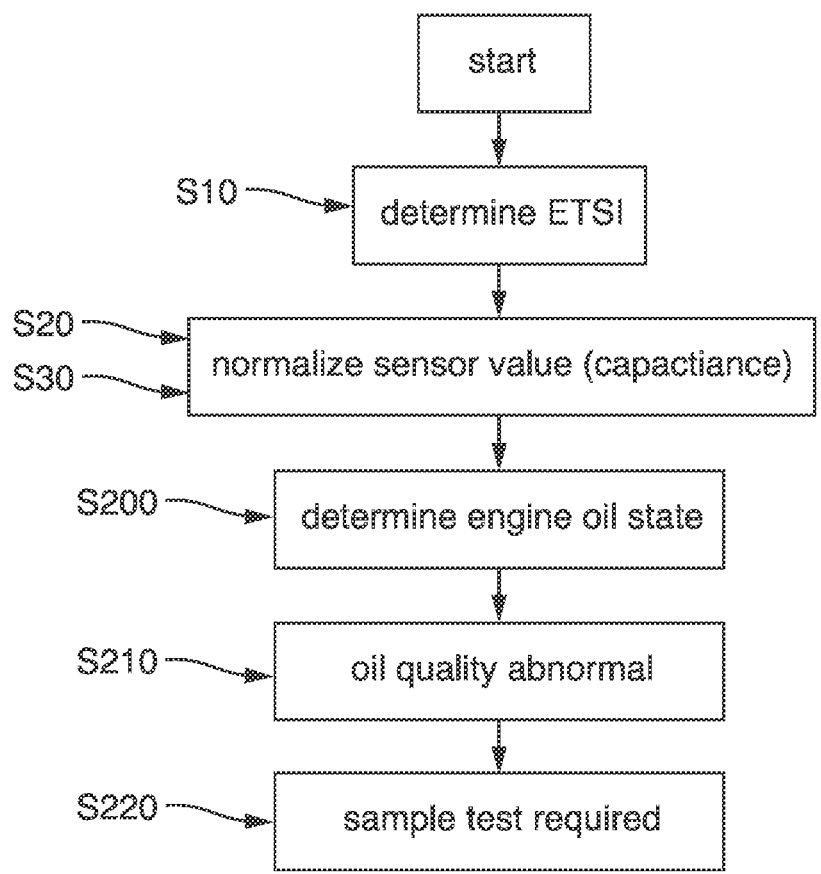
FIG. 5 schematically shows a flow diagram illustrating a method of determining an abnormal lubrication oil condition according to a first embodiment.
Figure 6:
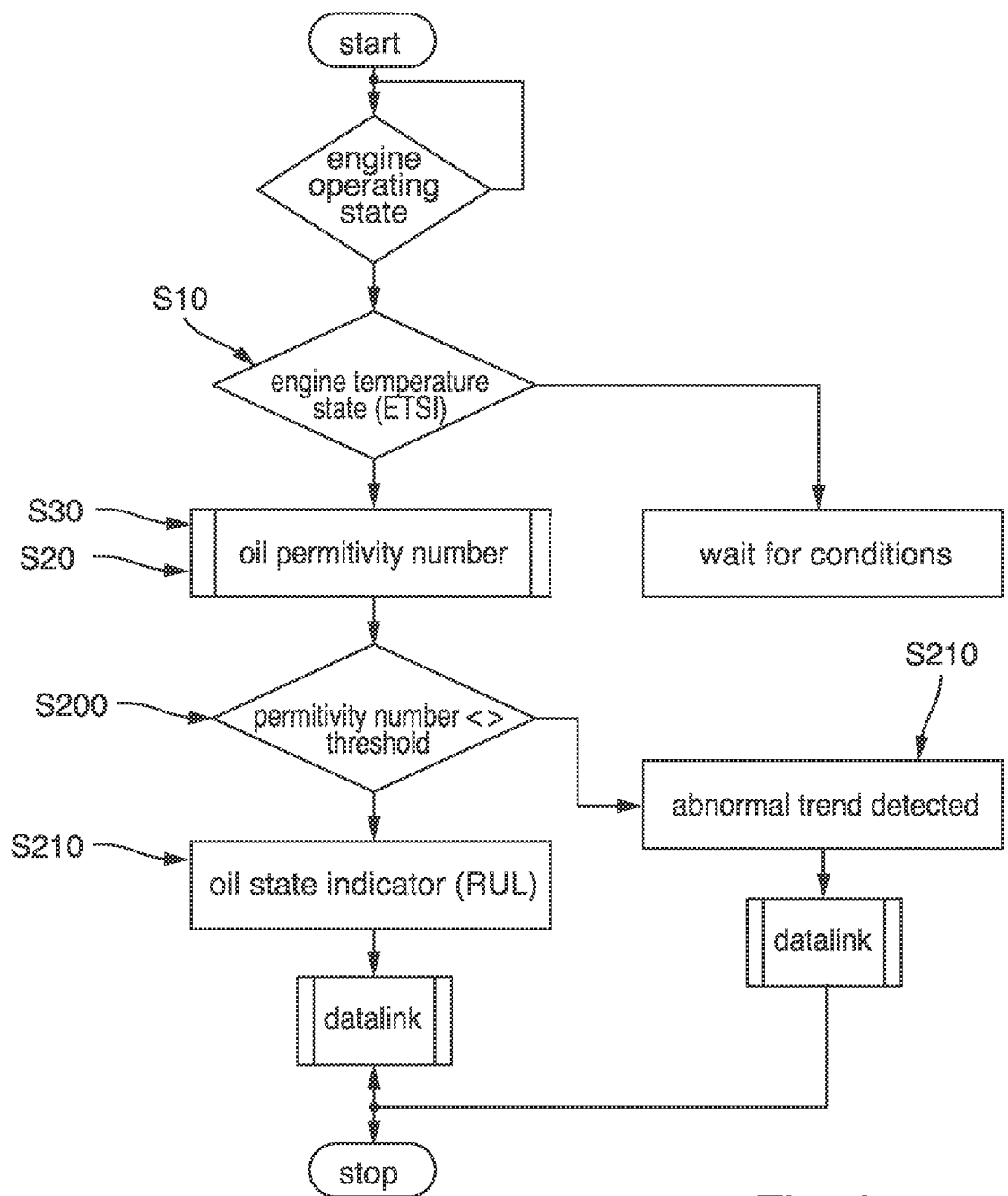
FIG. 6 schematically shows a diagram illustrating a method of determining an abnormal lubrication oil condition according to a second embodiment.

FIG. 5 schematically shows a flow diagram illustrating a method of determining an abnormal lubrication oil condition according to a first embodiment. Therein, upon starting the engine an engine state indicator, an ETSI information is determined, meaning the step of retrieving S10 of a lubrication oil temperature information is conducted. In this specific case, the lubrication oil temperature information is retrieved in the form of an engine temperature state indicator ETSI information as set forth above in the discussion of FIG. 1. At the same time or during a subsequent step, the lubrication oil level information is retrieved in a retrieving step S20 from a capacitance sensor.

In the normalization step S30, a lubrication oil permittivity number is obtained in order to detect abnormalities in lubrication oil degradation. The sensor capacitance voltage output is used to sense the lubrication oil permittivity number. The sense of value is normalized over lubrication oil temperature (ETSI) within the normalizing step S30. Subsequently, in a determining step S200, a lubrication oil permittivity number is obtained from a predetermined reference degradation map. In the identifying step S210, it is determined if the lubrication oil permittivity number is outside an acceptable threshold of the reference degradation map or not.

The lubrication oil permittivity number takes the current condition of several individual physical properties of the lubrication oil into account. It is based on a physical signal capacitance sensor value which may subsequently be normalized over lubrication oil temperature information.

The capacitance lubrication oil level sensor may be configured such that it is able to measure various performance parameters like viscosity, wear particle amount, total acid number or pH value by a change of permittivity.

Permittivity, also known as the inductivity, may be calculated by measuring the capacitance of the lubrication oil level sensor in the form of a capacitance sensor.

As a general rule, wear particles, total acid number or pH value, oxidation water contamination or particle contamination lead to a different permittivity with increasing contamination.

Before conducting the identifying step S210, a design of experiments DOE may be provided to study the influences on lubrication oil permittivity and the capacitance which is provided by the capacitance sensor. Further, the latter has to be conducted for various lubrication oil samples at different temperatures and degradation stages separately. This data is used to develop a physical model in the shape of one or more look-up tables. In return, the values provided within the look-up tables may be used as factors to normalize the effect of various parameters in order to observe explicitly the effect of degradation on the capacitance. Again, as an output of this look-up table, the lubrication oil permittivity number is obtained. To this end, a predefined map for acceptable permittivity numbers may be provided based on experimental trials.

Further, a continuous check may be performed to determine, if the determined real-time permittivity number is within acceptable thresholds or is deviating from its desired curve. In case that an abnormal trend is detected, a lubrication oil sample test request is triggered in a step of indicating S220 that a sample test is required.

Figure 7:
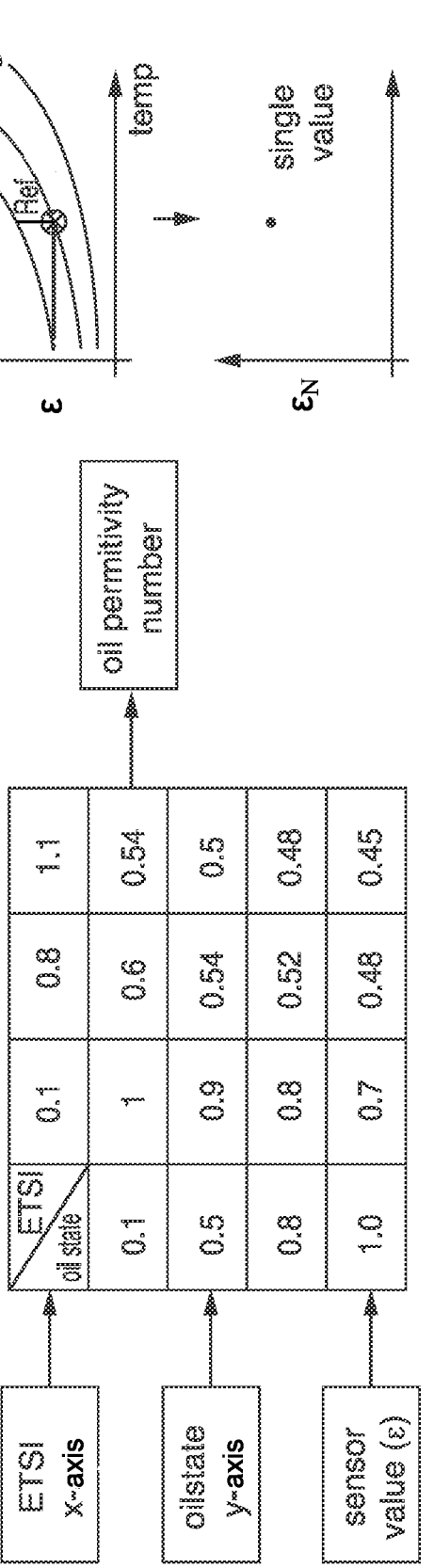
FIG. 7 schematically shows a diagram illustrating obtaining a lubrication oil permittivity number.

FIG. 7 schematically shows a diagram illustrating obtaining a lubrication oil permittivity number by means of a look-up table. As set forth above, normalization occurs during the normalization step S30.

The look-up table comprises a first row containing engine temperature state indicator ETSI values. In the second row, the lubrication oil permittivity number is listed for a given ETSI value. In the third row, reference values from a lubrication oil state are provided for each ETSI value, wherein the default state of the lubrication oil state is set to 0.1. In the lowest row, sensor values c are provided corresponding to a certain ETSI value. In order to retrieve a temperature that is normalized over the lubrication oil permittivity number, the sensor values c are plotted against temperature in a first step. In a second step, the sensor values c are normalized against temperature by multiplying the lubrication oil state with the ETSI value. As a result, a single value will be obtained which is called $\varepsilon_N$. Thereby, the default state of the lubrication oil state is set to 0.1 and the default value of the ETSI is set to 1.0. The initial oil state may be updated after an oil change or oil addition by a separate algorithm. The default oil state may be defined as 0.1.

FIG. 8 schematically shows a diagram illustrating determining an abnormal lubrication oil condition. In order to determine an abnormal lubrication oil state, a reference degradation map is required. The reference degradation map may comprise a first row, covering values representing lubrication oil in operation hours and a second row covering lubrication oil permittivity numbers for a given operation hours. For each lubrication oil, such a reference degradation map must be determined experimentally in order to check various SAE40 lubrication oils. Further, various applications must be checked in order to find suitable deviation windows.

Determining if the lubrication oil is in an abnormal state may be explained on behalf of the plot depicted in FIG. 8. According to this plot, normalized sensor values $\varepsilon_N$ are plotted against operating hours. In combination with the above introduced reference degradation map, an expected curve (solid line) as well as allowed deviation curves (dashed lines) are obtained. The curves shown in the plot may be obtained via a regression functions of the data points stored in the degradation map and are based on experimentally determined conditions of a given lubrication oil.

In view thereof, if a lubrication oil permittivity number is detected that lies outside the illustrated threshold, hence following an abnormal trend to such an extent that the allowed deviation curve is surpassed, an abnormal lubrication oil state detection is indicated.

It will be obvious for a person skilled in the art that these embodiments and items only depict examples of a plurality of possibilities. Hence, the embodiments shown here should not be understood to form a limitation of these features and configurations. Any possible combination and configuration of the described features can be chosen according to the scope of the invention.

A method may be provided for determining the lubrication oil condition for stationary gas engine. The method comprises the step of:
retrieving lubrication oil temperature information and the step of
retrieving a lubrication oil level information from a lubrication oil level sensor.

The lubrication oil level sensor is a capacitance sensor. Further, the method comprises the step of:

normalizing the lubrication oil level information over the lubrication oil temperature information.

Upon starting an engine, the operating state of the engine may be monitored. Once the engine is into running state, the method of determining a lubrication oil condition may be active and may proceed to retrieve a lubrication oil temperature information and a lubrication oil level information. Whereas the lubrication oil temperature information may be retrieved from a temperature sensor, the lubrication oil level information may be retrieved from a lubrication oil level sensor which is a capacitance sensor.

Like temperature sensors, lubrication oil level sensors are readily available in stationary gas engines. More detailed, in state of the art stationary gas engines of the applicant, temperature sensors and a lubrication oil level sensor of the capacitance type are provided. Such lubrication oil level sensors are a standard component providing an output information corresponding to lubrication oil levels within a stationary gas engine or a lubrication oil level reservoir.

Usually, stationary gas engines comprise additional sensors for determining a lubrication oil condition. However, providing such additional sensors is associated with higher costs and increased complexity.

Capacitance sensors are widely used to detect a change in physical properties of a liquid medium. Simply speaking, capacitance sensors according to the present disclosure may detect a change of conductivity of a medium. To this end, the sensor may comprise two adjacent probes that are electrically conductive and in contact with the medium to be measured. During measurement, a voltage may be applied to said probes. If the property or the mixture of the contacting medium changes, the electrical conductivity of said contacting medium changes. The change in conductivity can thus be measured by a change in voltage measured at the sensor probes and corresponds to a change in medium contacting the probes.

Hence, using such a capacitance sensor that is already implemented in the engine represents a cost-effective and simple source of information on the basis of which the method of determining a lubrication oil condition may be executed.

By normalizing the lubrication oil level information over the lubrication oil temperature information in the normalization step, a robust method may be provided that, in addition, may be cost-effectively implemented.

The proposed method may be used in stationary gas engines as well as lubrication oil reservoirs for stationary gas engines. However, the method is not limited to this application and may be used in connection with any engine, for example a stationary or mobile engine, a gaseous propellant or liquid propellant driven engine, or a reciprocating or a continuously operating engine.

The retrieved lubrication oil temperature information and/or the retrieved lubrication oil level information may be understood as a signal which is retrieved directly or indirectly from a sensor.

Specifically, the lubrication oil temperature information may be provided as an engine temperature state indicator ETSI information which is retrieved from ETSI look-up table, preferably wherein the look-up table comprises an ETSI map which is populated based on a predetermined engines cooling circuit design. Such engine temperature state indicator information may be used as an enabler for the normalization step. In the broadest sense, the ETSI information may be a value that is referring to a temperature state in a dimensionless representation.

As an example, the ETSI look-up table may comprise a header row comprising reference engine lubrication oil temperature values as well as at least one subsequent row comprising dimensionless values corresponding to the reference engine lubrication oil temperature values. In other words, instead of using the lubrication oil temperature values directly as lubrication oil temperature information, the latter is taken indirectly from an ETSI look-up table in the form of a non-dimensional ETSI value. The ETSI map of the ETSI look-up table may be populated for a range of different reference temperatures and for a given lubrication oil.

Alternatively, the ETSI look-up table may also comprise information for different lubrication oils. In this case, it may be required to retrieve information regarding the lubrication oil currently used in the engine or reservoir.

In a further development, the method may further comprise the step of waiting until the lubrication oil temperature information reaches a predetermined temperature threshold after starting the engine. Thereby it can be avoided that the method continuously produces false alarms for example due to the engine not being in a steady-state operation mode. Further, the temperature threshold may be altered depending on the type of lubrication oil used in the engine. Accordingly, the temperature threshold may be altered or adjusted to fit to a new type of lubrication oil. Changing the temperature threshold does not require any changes to the implemented algorithm of the method.

The lubrication oil temperature information may be information retrieved from an engine and/or a lubrication oil reservoir. Likewise, the temperature threshold may comprise temperature data taken from the engine or a lubrication oil reservoir.

In the following, determining a lubrication oil consumption by means of the disclosed method will be described. Hence, the lubrication oil condition may comprise a condition representing a lubrication oil consumption. To this end, the method may further comprise the steps of:
  waiting for a counter to be active,
  storing at least one lubrication oil level information,
  determining a difference in lubrication oil level at a predetermined time interval and storing said difference, and
  determining the lubrication oil consumption by utilizing a predetermined lubrication oil correlation.

Preferably, the counter may be a function of time and may be calibrated to have values stored and processed at a desired time interval. Further, the at least one lubrication oil level information stored may be in the form of a sensor output. Determining a difference in lubrication oil level may be determined at a predetermined time interval and may also be stored. The predetermined lubrication oil correlation may comprise utilizing lubrication oil properties like density, lubrication oil type and engine lubrication oil pan details. The correlation may comprise a dependency between engine lubrication oil level to lubrication oil volume and further volume to weight. Further, a power produced counter may be provided using a generator power signal and operating hours. By that, the lubrication oil consumption may be calculated on the basis of g/kWh.

In a further development, in the storing step, the at least one lubrication oil level information is stored in a ring storage, preferably wherein the ring storage can save n values at a time, preferably wherein the ring storage works on a first in first out principle. By that, it can be guaranteed that sufficient data points are available in the storage.

Further, it can be guaranteed that the correct data points are used in the processing of the lubrication oil information.

Alternatively or additionally, a difference in lubrication oil level may be determined at a predefined time interval and the determined difference in lubrication oil level may also be stored. Thereby, a consistent set of data may be acquired and also be used for data postprocessing purposes.

In another embodiment, the lubrication oil condition may comprise a condition representing a lubrication oil change detection. Therein, the method may further comprise the steps of:

storing at least one lubrication oil level information, monitoring change in lubrication oil level between an engine stop condition to a subsequent engine start condition, and wherein, if the lubrication oil level fell below a predetermined threshold during the monitoring step, indicating (S160) that a lubrication oil change had occurred, wherein, if a lubrication oil change was detected, updating (S170) a counter for a subsequent lubrication oil change.

According to the lubrication oil condition there is determined by means of this algorithm, it shall be indicated if a lubrication oil change occurred during a shutdown in a subsequent start of an engine. Thereby, a failsafe and convenient way of updating service intervals may be provided.

Due to the nature of a lubrication oil change, the indication that a lubrication oil change had occurred requires that the engine and/or the lubrication oil reservoir had been empty during the time of a shutdown and the subsequent start of the engine. As an example, a lubrication oil change could be confirmed if the lubrication oil level engine one value fell below 10% of the initial lubrication oil level in the engine and/or the lubrication oil reservoir. In any case, said value may conveniently be selected such that potential residual lubrication oil, remaining in the engine or the reservoir, may be taken into account without leading to false outcomes.

In a preferred development, the method may further comprise a step of checking the lubrication oil level sensor for any active diagnostics or anomalies in order to qualify the lubrication oil change indication step. As such, false alarms may be avoided. Being able to rule out any lubrication oil level sensor outage or malfunctioning—which could potentially trigger a signal that is equal to the signal of an empty engine or reservoir—the method of determining if a lubrication oil change occurred may always be activated.

According to another embodiment, the lubrication oil condition may comprise a condition representing an abnormal lubrication oil condition. To this end, the method may further comprise the steps of:

determining an engine lubrication oil state; and identifying that the lubrication oil condition is an abnormal lubrication oil condition, preferably comprising a subsequent step of indicating that a sample test is required.

In this way, any abnormal lubrication oil condition that can be detected by means of the capacitance lubrication oil level sensor may be determined using only lubrication oil temperature information and lubrication oil level information. In other words, no dedicated liquid lubrication oil quality sensor needs to be installed in the engine or in the lubrication oil reservoir. Thereby, a convenient, cheap and robust method of detecting an abnormal lubrication oil condition may be provided.

According to a further development, in the normalization step, a lubrication oil permittivity number is obtained, in the determining step, a lubrication oil permittivity number is obtained from a predetermined reference degradation map. Further, in the identifying step, is determined if the lubrication oil permittivity number lies outside an acceptable threshold of the reference degradation map or not.

It is known in the state of the art that conventional lubrication oil level sensors of the capacitance type may detect a wide range of changes in physical properties as well as the presence of contaminants in a lubrication oil. As an example, it is known that the acidic value, the iron content as well as moisture content within a lubrication oil lead to an increased dielectric coefficient. In view thereof, a change in dielectric coefficient may be correlated with abnormal states.

According to a further embodiment, the reference degradation map may comprise a look-up table including degradation curves as a function of operating hours, preferably wherein the degradation curves represent experimentally determined conditions of the lubrication oil. In order to quantitative the lubricant oil condition, changes in the dielectric coefficient, represented as changes in lubrication oil level sensor voltages, may be identified in specific degradation maps. Thus, a predetermined degradation over time for a given lubricating lubrication oil may be provided. This has the advantage that if one type of lubrication oil is replaced by another type of lubrication oil, only the degradation map needs to be updated and not the algorithm or method itself.

According to a further embodiment, the degradation curves may be based on a regression function. Regression functions allow a convenient interpolation of individual experimentally obtained data points. To this end, a continuous function may be achieved even for data ranges where there is no specific experimentally acquired data point. This saves time and efforts for populating the degradation map.

Preferably, the lubrication oil level information may be provided as a processed signal, in particular a pulse-width-modulated PWM signal, as an output information corresponding to a given lubrication oil level. A processed signal may be any signal that is modified, altered, multiplied, filtered, cut, separated, or selected with reference to the raw signal provided by the probes. Using a processed signal has the advantage that the at times chaotic raw signals provided by the probes may be processed prior to utilizing that signal in subsequent use cases. Thus, the obtained lubrication oil level information may be processed and analyzed more conveniently. To this end, pulse-width-modulation (PWM) is a method of reducing the average power delivered by an electrical signal, by effectively separating it into discrete parts. Using a pulse-width-modulated PWM signal has the advantage that capacitive pulses generated by contaminants in the lubricating lubrication oil, by droplets or by a sudden change of filling height are softened within the signal output. Thus, the obtained lubrication oil level information may be processed and analyzed more conveniently.

In addition, a stationary gas engine comprising at least one lubrication oil temperature sensor and at least one lubrication oil level sensor of a capacitance sensor type and a computing device and a non-transitory computer-readable storage medium encoded with data and instructions that, when executed by the computing device, cause the computing device to carry out the method described above. Accordingly, technical features which are described in connection with the method of determining a lubrication oil condition may also relate and be applied to the proposed stationary gas engine, and vice versa.

Accordingly, technical features which are described in connection with the above method may also relate and be applied to the proposed construction machine and/or the computer system, and vice versa.

Accordingly, technical features which are described in connection with the above method may also relate and be applied to the proposed construction machine and/or the computer system, and vice versa.

INDUSTRIAL APPLICABILITY

With reference to the Figures, a method of determining a lubrication oil condition as mentioned above is applicable in any suitable engine, such as a stationary gas.

What is claimed is:

1. A lubrication oil condition management method carried out by a lubrication oil condition monitoring system of a stationary gas engine,
   wherein the lubrication oil condition monitoring system comprises:
   a temperature sensor in the stationary gas engine,
   a capacitance sensor configured to measure a lubrication oil level, and
   an engine temperature state indicator (ETSI) look-up table that comprises an ETSI map populated based on a predetermined engine cooling circuit design; and
   wherein the lubrication oil condition management method comprises:
   acquiring a temperature value from the temperature sensor in the stationary gas engine;
   retrieving, by applying the temperature value to the ETSI look-up table, a lubrication oil temperature information as a dimensionless temperature reference value;
   retrieving a lubrication oil level information from a lubrication oil level signal provided by the capacitance sensor;
   determining a lubrication oil condition of the stationary gas engine using a permittivity value obtained using the lubrication oil level signal that is normalized over the lubrication oil temperature information, wherein the determining is carried out by applying the lubrication oil level signal that is normalized over the lubrication oil temperature information, to a degradation map; and
   initiating, by the lubrication oil condition monitoring system in accordance with the determining, a remedial operation with respect to the lubrication oil of the stationary gas engine.

2. The method according to claim 1, further comprising waiting until the lubrication oil temperature information reaches a predetermined temperature threshold value after starting the engine.

3. The method according to claim 2, wherein the method further comprises determining a condition representing a lubrication oil consumption
   by:
   waiting for a counter to be active;
   storing at least one lubrication oil level information value;
   determining a difference in lubrication oil level at a predetermined time interval and storing the difference; and
   determining the lubrication oil consumption by utilizing a predetermined lubrication oil correlation comprising (a) a dependency between engine lubrication oil level to lubrication oil volume and (b) a relationship of lubrication oil volume to weight.

4. The method according to claim 3, wherein, in the storing step, the at least one lubrication oil level information is stored in a ring storage, wherein the ring storage can save n values at a time, wherein the ring storage is configured to work on a first in-first out principle.

5. The method according to claim 2, wherein the method further comprises determining a condition representing a lubrication oil change detection by:
   storing at least one lubrication oil level information;
   monitoring change in lubrication oil level between an engine stop condition to a subsequent engine start condition; and
   wherein the method further comprises, in accordance with the lubrication oil level falling below a predetermined threshold during the monitoring step, performing:
   indicating that a lubrication oil change had occurred, and
   updating a counter for a subsequent lubrication oil change.

6. The method according to claim 5, further comprising checking the lubrication oil level sensor for any active diagnostics or anomalies.

7. The method according to claim 1, wherein the remedial operation is initiated in accordance with the permittivity value being
   outside an acceptable range of permittivity values specified by a reference degradation map.

8. The method according to claim 7, wherein the reference degradation map comprises a look-up table including degradation curves as a function of operating hours, wherein the degradation curves represent experimentally determined conditions of the lubrication oil.

9. The method according to claim 8, wherein the degradation curves are based on a regression function.

10. The method according to claim 7, wherein the reference degradation map is designed such that it considers the impact of lubrication oil lubrication contaminants of at least one of wear particles, oxidation particles, acid number, pH value and water content.

11. The method according to claim 1, wherein the lubrication oil level information is provided as a pulse-width-modulated (PWM) signal corresponding to a given lubrication oil level.

12. Stationary gas engine including a lubrication oil condition monitoring system comprising:
    a temperature sensor in the stationary gas engine,
    a capacitance sensor configured to measure a lubrication oil level, and
    an engine temperature state indicator (ETSI) look-up table that comprises an ETSI map populated based on a predetermined engine cooling circuit design;
    a computing device; and
    a non-transitory computer-readable storage medium encoded with data and instructions that, when executed by the computing device, cause the lubrication oil condition monitoring system to carry out a lubrication oil condition management method comprising:
    acquiring a temperature value from the temperature sensor in the stationary gas engine;
    retrieving, by applying the temperature value to the ETSI look-up table, a lubrication oil temperature information as a dimensionless temperature reference value;

retrieving a lubrication oil level information from a lubrication oil level signal provided by the capacitance sensor;

determining a lubrication oil condition of the stationary gas engine using a permittivity value obtained using the lubrication oil level signal that is normalized over the lubrication oil temperature information, wherein the determining is carried out by applying the lubrication oil level signal that is normalized over the lubrication oil temperature information, to a degradation map; and initiating, by the lubrication oil condition monitoring system in accordance with the determining, a remedial operation with respect to the lubrication oil of the stationary gas engine.

13. The stationary gas engine according to claim 12, wherein the method further comprises waiting until the lubrication oil temperature information reaches a predetermined temperature threshold value after starting the engine.

14. The stationary gas engine according to claim 13, wherein the method further comprises determining a condition representing a lubrication oil consumption by:

waiting for a counter to be active;

storing at least one lubrication oil level information value;

determining a difference in lubrication oil level at a predetermined time interval and storing the difference; and determining the lubrication oil consumption by utilizing a predetermined lubrication oil correlation comprising (a) a dependency between engine lubrication oil level to lubrication oil volume and (b) a relationship of lubrication oil volume to weight.

15. The stationary gas engine according to claim 14, wherein, in the storing step, the at least one lubrication oil level information is stored in a ring storage, wherein the ring storage can save n values at a time, wherein the ring storage is configured to work on a first in-first out principle.

16. The stationary gas engine according to claim 13, wherein the method further comprises determining a condition representing a lubrication oil change detection by:

storing at least one lubrication oil level information;

monitoring change in lubrication oil level between an engine stop condition to a subsequent engine start condition; and wherein the method further comprises, in accordance with the lubrication oil level falling below a predetermined threshold during the monitoring step, performing:

indicating that a lubrication oil change had occurred, and updating a counter for a subsequent lubrication oil change.

17. The stationary gas engine according to claim 16, further comprising checking the lubrication oil level sensor for any active diagnostics or anomalies.

18. The stationary gas engine according to claim 12, wherein the remedial operation is initiated in accordance with the permittivity value being outside an acceptable range of permittivity values specified by a reference degradation map.

19. The stationary gas engine according to claim 18, wherein the reference degradation map comprises a look-up table including degradation curves as a function of operating hours, wherein the degradation curves represent experimentally determined conditions of the lubrication oil.

20. The stationary gas engine according to claim 19, wherein the degradation curves are based on a regression function.

* * * * *